(12) United States Patent
Halleen et al.

(10) Patent No.: US 6,248,544 B1
(45) Date of Patent: Jun. 19, 2001

(54) METHOD OF MEASURING BONE RESORPTION RATE

(76) Inventors: Jussi Halleen, Uudenmaankatu 8 B 30, FIN-20500, Turku; Kalervo Väänänen, Peikontie 2 D 43, FIN-90550, Oulu, both of (FI)

(*) Notice: Subject to any disclaimer, the term of this patent is extended or adjusted under 35 U.S.C. 154(b) by 0 days.

(21) Appl. No.: 09/281,092

(22) Filed: Mar. 30, 1999

Related U.S. Application Data

(60) Provisional application No. 60/080,283, filed on Apr. 1, 1998, now abandoned.

(51) Int. Cl.$^7$ .................. G01N 33/573; G01N 21/76
(52) U.S. Cl. .................. 435/7.4; 435/7.1; 435/7.5; 435/372; 435/21; 435/7.8; 435/7.95; 435/173.1; 436/501; 436/536; 436/537; 436/546; 436/548; 436/163; 436/164; 436/172; 436/56; 436/811
(58) Field of Search .................. 435/7.1, 7.5, 7.4, 435/325, 366, 372, 21, 7.8, 7.95, 173.1; 424/184.1, 185.1, 193.1; 436/548, 172, 163, 164, 501, 536, 537, 546, 56, 811

(56) References Cited

PUBLICATIONS

Gaucher Disease: A Century of Delineation and Research, pp. 267–278, "Biochemical Properties of the Tartrate–Resistant Acid Phosphatase Activity in Gaucher Disease", Kwok–Wai Lan et al.

Journal of Bone and Mineral Research, vol. 11, No. 10, 1996, "Tartrate–Resistant Acid Phosphatase from human Bone: Purification and Development of an Immunoassay", Jussi Halleen et al.

Clin. Chem.24/7, 1105–1108(1978), Biochemical Properties of Tartrate–Resistant Acid Phosphatase in Serum of Adults and Children, William K.W. Lam et al.

Clin. Chem. 41/5, 879–686(1985), "Immunoassay of a Tartrate–Resistant Acid Phosphatase in Serum", Chi K. Cheung et al.

Journal of Clinical Endocrinology and Metabolism, vol. 71, No. 2, pp. 442–451, "Development of an Immunoassay for Human Serum Osteoclastic Tartrate–Resistant Acid Phosphatase", Marius E. Kraenzlin et al.

Development 122, 3151–3162(1996), "Mice lacking tartrate–resistant acid phosphatase (Acp 5) have disrupted endochondral ossification and mild osteopetrosis", Alison R. Hayman et al.

Lau et al., Evidence that TRAP from Osteoclastomas and Hairy cell Leukemia spleen are members of the Multigene Family, Int J Biochem 23 (11): 1237–1244 (1991), Nov. 30, 1990.*

Lam et al., Comparison of Prostatic and Nonprostatic Acid Phosphatase, Annals of the New York Academy of Sciences 390: 1–15 (1990, Nov. 30, 1990.*

Chemical Abstracts, vol. 123, No. 21, 11/95 Abstract No. 282976e Chamberlain et al p. 917 col. 1 XP00200531 & Clin Chem., vol. 41, No. 10, 1995, pp 1495–1499.

(List continued on next page.)

Primary Examiner—Long V. Le
Assistant Examiner—Gailene R. Gabel
(74) Attorney, Agent, or Firm—Nixon & Vanderhye P.C.

(57) ABSTRACT

Tartrate-resistant acid phosphatase (TRAP) has been used as a marker for bone resorption. However, there are two forms of said enzyme in the body: TRAP 5a and TRAP 5b, of which TRAP 5b is a much more specific marker. The present invention is directed to an immunoassay for measuring the bone resorption rate, which methods enables the specific determination of TRAP 5b, whereby the amount of TRAP 5b reflects the bone resorption rate. The method is useful in diagnosing disorders associated with a change in the bone resorption rate, such as osteoporosis. Methods of screening for susceptibility to such disorders, and method of monitoring the effect of treatment are also provided. Further a test-kit useful in said methods is provided.

11 Claims, 1 Drawing Sheet

OTHER PUBLICATIONS

Chemical Abstracts, vol. 127, No. 3, 7/97 abstract No. 32591a, Janckila et al p. 491, col. 1, XP002900532 abstract & Hybridoma, vol. 16, No. 2, 1997, pp 175–182.

Chemical Abstracts, vol. 129, No. 6 8/98 Abstract No. 64633y Halleen et al p. 304, col. 2 XP002900533 abstract & J. Bone Miner. Res., vol. 13, No. 4, 1998, pp 683–687.

Chemical Abstracts, vol. 117, No. 5, 8/92 abstract No. 41370y, Alam et al p. 202, column 1; XP002900534 abstract & Endocrinology vol. 130, No. 6, 1992, pp. 3617–3724.

Chemical Abstracts, vol. 126, No. 3, 1/97 abstract No. 29683f Fukuoka p. 402, col. 2; XP002900535 Abstract & Horumon to Rinsho, vol. 44, No. 11, 1996, pp 1145–1149.

Chemical Abstracts, vol. 128, No. 23, 6/98 abstract No. 280012s, Nakanishi et al p. 189, col. 1; XP002900536 & Clin. Chem., vol. 44, No. 2, 1998, pp. 221–225.

Lam et al., "Comparison of Prostatic and Nonprostatic Acid Phosphatase", Annals NY Academy Sciences, 1982, pp. 1–15.

Halleen et al., "Tartrate–Resistant Acid Phosphatase from Human Bone: Purification and Development of an Immunassay", Journal of Bone and Mineral Research, vol. 11, No. 10, 1996.

* cited by examiner

METHOD OF MEASURING BONE RESORPTION RATE

This application claims the benefit of U.S. Provisional Application No. 60/080,283, filed Apr. 1, 1998 now, abandoned.

FIELD OF THE INVENTION

The present invention relates to a method of measuring the bone resorption rate, and particularly to an immunoassay therefor. The invention further relates to a method of diagnosing a disorder associated with a change in the bone resorption rate such as osteoporosis, and to a test kit useful in said methods. The invention also relates to a method of monitoring the effect of a drug for treating a disorder associated with an increase in the bone resorption rate in a subject and to a method of screening subjects for susceptability to said disorder. The use of a specific marker for the bone resorption rate is disclosed.

TECHNICAL BACKGROUND

There are several disorders associated with changes in the bone resorption rate, the most widely spread being osteoporosis, a disease common in postmenopausal women. Osteoporosis is caused by loss of bone mass resulting in a weak skeleton, which is susceptible to fractures. The treatment of fractures and other maladies caused by osteoporosis is expensive to society, not to mention the suffering of the patients. There is therefore a need for diagnosing persons suffering from osteoporosis in order to prevent severe consequences thereof. Osteoporosis has been successfully treated e.g. by estrogen replacement or biphosphonate treatment.

There are several instruments and methods for measuring bone density. However, the apparatuses and operations used are expensive, because they require much space and personnel and the measuring is slow and the patient has to be present. Since the age-class distribution of the population is becoming more unfavourable as far as osteoporosis is concerned, it is important to develop specific, rapid, simple and cheap in vitro methods for measuring the bone resorption rate.

Bone consists substantially of two major cell types, the bone forming osteoblasts and the bone resorbing osteoclasts. Normally these two cell types are in balance, the osteoclasts resorb the same amount of bone as the osteoblasts form. Osteoporosis is the result of an increased activity of the osteoclasts resulting in a disorder where the osteoclasts resorb more bone than the osteoblasts produce.

Tartrate-resistant acid phosphatase (TRAP, EC 3.1.3.2.) belongs to the type 5 class of acid phosphatases according to its electrophoretic mobility and is therefore also called type 5 acid phosphatase. At least seven acid phosphatases can be identified by acidic polyacrylamide gel electrophoresis. The most acidic of these is the band 5 acid phosphatase (Acp5), and it is the only one resistant to inhibition by tartrate, therefore the name TRAP. This enzyme is a basic glycoprotein that contains a spin-coupled iron unit at the active site of the molecule. The binuclear iron unit of TRAP contains two ferric ions, which make the protein purple, and it is also called purple acid phosphatase. This protein has a molecular weight of 32 kd. When the enzyme is reduced e.g. with β-mercaptoethanol, one of the ferric ions is reduced and the enzyme becomes pink. TRAP can function as a protein tyrosine phosphatase in vitro and its amino acid sequence contains regions homologous to those of phosphoprotein phosphatases. However, its natural substrates are still unknown.

The tyrosine phosphorylation is an important regulation mechanism for the function and differentiation of many cells. TRAP is believed to play an important role in the regulation of the function of the osteoclasts. It is known that TRAP is capable of producing hydroxyl radicals, which are capable of reacting and destroying chemical compounds in nature. The osteoclasts produce free oxygen radicals during bone resorption and it is evident that they are significant in bone resorption. Their origin is unknown, but it seems that at least part of the hydroxyl radicals is formed by TRAP. Both cell types normally containing TRAP i.e. the osteoclasts and the alveolar macrophages take up chemical compounds and degrade them. This common feature strongly supports the assumption that TRAP takes part in bone resorption.

Hayman, A. R. et al. (Development 122:3151–3162, 1996) have investigated the role of TRAP by targeted disruption of the TRAP gene in mice. They found that mice lacking the gene had disrupted endochondral ossification and mild osteopetrosis. They concluded that TRAP is required for normal mineralization of cartilage in developing bones and that it also maintains integrity and turnover of the adult skeleton by a critical contribution to bone matrix resorption.

The only normal human cells that contain significant amounts of TRAP are the osteoclasts and activated macrophages. In certain pathological conditions TRAP can also be found in other cells. It has been found that TRAP is secreted from the osteoclasts into the blood circulation during bone resorption. The concentration of TRAP in serum has therefore been suggested as a marker of bone resorption, and it has been found that the concentration of TRAP in serum correlates with the bone resorption rate (Kraenzlin M. E. et al. Journal of Clinical Endocrinology and Metabolism 71(2):442–451, 1990; Cheung C. K. et al. Clin. Chem. 41(5):679–686, 1995; Chamberlain P. et al. Clin. Chem. 41(10):1495–1499, 1995 and Halleen J. et al. Journal of Bone and Mineral Research 11(10):1444–1452, 1996).

In 1978 Lam W. K. W. et al. (Clin. Chem. 24(7):1105–1108, 1978) reported a study of the biochemical properties of TRAP in the serum of adults and children. By an improved electrophoretic method they found two distinct TRAP bands, which they designated 5a and 5b. TRAP 5a had a lower pH optimum than TRAP 5b. Both enzyme forms TRAP 5a and TRAP 5b were found in human sera. The amount of TRAP 5a was found to be constant in adults and children, but the amount of TRAP 5b was elevated in children.

In another paper (Chen et al., Clin. Chem. 25, 719–722, 1979), the same group of investigators studied the significance of high acid phosphatase activity in the serum of normal children. They showed that serum TRAP activity, corresponding to band 5, was present in giant-cell tumors, and not in osteogenic sarcomas, suggesting that TRAP would be derived from osteoclasts.

W. K. W. Lam et al. (Clin. Biochem. 14, 177–181, 1981) isolated TRAP from the serum and spleen of patients affected by Gaucher's disease. They showed that Gaucher's disease serum contained band 5b, whereas Gaucher's disease spleen contained band 5a. Bands 5a and 5b had identical protein structure, and removal of carbohydrate from 5a by sialidase converted it to 5b, suggesting that the only structural difference between 5a and 5b would be the presence of sialic acid residues in 5a that are not present in 5b. The pH-optima of the two forms was different, being 5.0 for 5a, and 5.5–6.0 for 5b.

W. K. W. Lam and R. J. Desnick (Progress in Clinical and Biological Research 95, 267–278, 1982) further studied the band 5 forms in Gaucher's disease. They also summarized the electrophoretic profiles of acid phosphatases in normal and pathologic specimen. They showed that in normal serum, trace amounts of both 5a and 5b are present, and they did not observe elevation of band 5a in any pathologic serum. Instead, they found elevated amounts of 5b in osteoclastic bone tumors, in the serum of patients with malignancies metastasized to bone, and in the serum of patients with Gaucher's disease. Based on these results the authors concluded that the results might suggest that the serum acid phosphatase level, and in particular the 5b form, is primarily dependent on the physiologic activity of the osteoclasts. However, they stated that further proof to support the hypothesis was needed. An other important observation from the paper is the authors statement that the enzymes (bands 5a and 5b) are closely related and antigenically identical. According to this statement, it would not be possible to develop an immunoassay that would specifically measure either 5a or 5b. After the year 1982, the origin of serum TRAP 5a and 5b has not been studied further, and the suggested osteoclastic origin of 5b has not been verified.

TRAP activity can be determined spectrophotometrically e.g. by feeding p-nitrophenyl phosphate (pNPP) as a substrate in the presence of tartrate, which inhibits most other acid phosphatases. However, this method is not very specific, and therefore more specific methods i.e. immunoassays have been developed for the determination of TRAP.

Stepan J. J et al. (Biochem. Biophys. Res. Commun. 165:1027–1034, 1989) and Kraenzlin M. E. et al. (Journal of Clinical Endocrinology and Metabolism 71(2):442–451, 1990) have developed an immunoassay for TRAP using polyclonal antibodies raised against TRAP purified from the spleen of a patient with hairy cell leukemia. They suggest that their assay may be useful in detecting patients with disorders in mineral metabolism.

Cheung C. K. et al. (Clin. Chem. 41(5):679–686, 1995) disclose an immunoassay of TRAP using polyclonal antibodies prepared against TRAP isolated from cord plasma. They found that the concentration of TRAP was significantly higher in children and in postmenopausal women and discuss the possibility of using TRAP as a marker in assessing bone turnover.

Polyclonal antibodies have also been prepared against TRAP isolated and purified form human bone. Again it was proved that children and postmenopausal women had elevated concentrations of TRAP in their sera (Halleen J. et al. Journal of Bone and Mineral Research 11(10):1444–1452, 1996).

Chamberlain P. et al. (Clin. Chem. 41(10):1495–1499, 1995) disclose a two-step serum immunoassay of TRAP using a pair of monoclonal antibodies, which had been raised against recombinantly produced TRAP. The monoclonals recognized different epitopes of TRAP and enabled a sensitive assay thereof.

All of the immunoassays published so far measure the total content of TRAP in serum. However, the present invention is based on the finding that TRAP 5b is a much more specific biochemical marker for bone resorption than total TRAP. In this connection it should be pointed out that the isoforms of TRAP reported by Stepan et al. and Kraenzlin et al. supra should not be confused with those reported by Lam et al. supra, although both are designated 5a and 5b.

One object of the present invention is therefore to take advantage of TRAP 5b as a specific marker for bone resorption.

Another object of the present invention is to provide a specific and simple method of measuring the bone resorption rate and especially to provide a diagnostic method of diagnosing a disorder associated with a significant change in the bone resorption rate, such as osteoporosis or other metabolic bone diseases, bone lesions, or bone metastases.

One further object of the present invention is to provide a method which enables monitoring bone resorption in subjects suspectible to or suffering from these disorders and to follow up the effect of treatment of them.

Still another object of the present invention is to provide a test kit useful in said methods.

SUMMARY OF THE INVENTION

The objects of the present invention can be achieved by using tartrate-resistant acid phosphatase 5b (TRAP 5b) as a marker for the bone resorption rate in an immunoassay.

The invention consequently provides an immunoassay for measuring the bone resorption rate in a subject, comprising determining tartrate-resistant acid phosphatase 5b (TRAP 5b) in a body fluid sample from said subject, whereby the amount of TRAP 5b reflects the bone resorption rate.

Especially there is provided an immunoassay for measuring the bone resorption rate in a subject, comprising the steps of (a) determining tartrate-resistant acid phosphatase 5b (TRAP 5b) in a body fluid sample from said subject by binding the TRAP present in the body fluid sample to an antibody that binds total TRAP (TRAP 5a and TRAP 5b), and (b) determining the bound TRAP activity at a pH between 5.7 and 6.3, whereby the amount of TRAP activity, which is mainly TRAP 5b, reflects the bone resorption rate.

The present invention also provides a method of diagnosing a disorder associated with a change in the bone resorption rate in a subject, said method comprising carrying out an immunoassay for determining tartrate-resistant acid phosphatase 5b (TRAP 5b) in a body fluid sample from said subject, whereby an abnormal amount of TRAP 5b indicates a disorder associated with a change in the bone resorption rate.

The invention further provides a method of monitoring the effect of a drug for treating a disorder associated with an increase in the bone resorption rate in a subject, said method comprising carrying out an immunoassay for determining tartrate-resistant acid phosphatase 5b (TRAP 5b) in body fluid samples of said subject, whereby a decreased amount of TRAP 5b indicates the effect of said drug.

Still further provided is a method of screening subjects for susceptibility to disorders associated with an increased bone resorption rate, said method comprising carrying out an immunoassay for determining tartrate-resistant acid phosphatase 5b (TRAP 5b) in body fluid samples of said subjects, whereby an elevated level of TRAP 5b indicates susceptibility to said disorder.

The invention further provides a test-kit comprising antibodies capable of distinguishing between tartrate-resistant acid phosphatase 5b (TRAP 5b) and tartrate-resistant acid phosphatase 5a (TRAP 5a). This test-kit is useful in carrying out the methods of the invention.

DETAILED DESCRIPTION OF THE INVENTION

Figure 1:
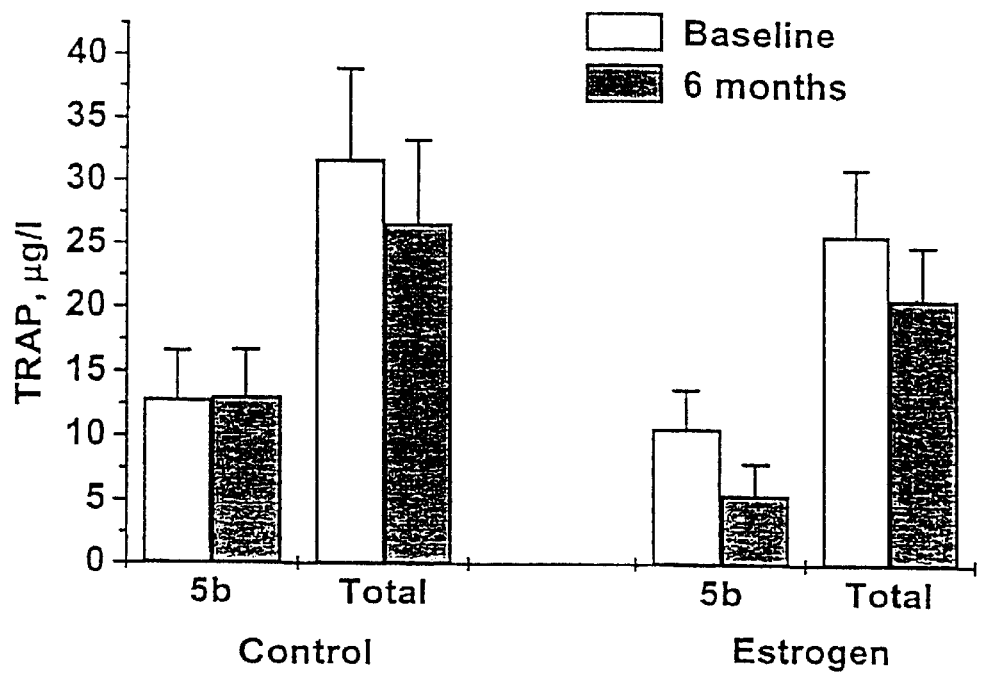
FIG. 1 shows the effect of estrogen treatment on the amount of total TRAP and TRAP 5b in sera.

When TRAP 5b is specifically determined instead of total TRAP in a body fluid sample of a subject, a significantly better correlation between the TRAP content and the bone resorption rate is achieved. It was unexpectedly found that it is possible to determine TRAP 5b specifically in an immunoassay by utilizing antibodies against TRAP. Surprisingly antibodies distinguishing between TRAP 5a and TRAP 5b could be found. However, the antibodies used in the present invention need not necessarily be either TRAP 5a or TRAP 5b specific, but antibodies recognizing total TRAP may also be used. In that case the distinction between the two enzyme forms is then achieved by other means after the reaction with non-specific anti-TRAP antibodies. It was e.g. found that the TRAP activity could be measured at a pH range, where practically all TRAP activity was derived from TRAP 5b. These findings may provide an improved method of diagnosing primary and secondary bone diseases associated with changes in the bone resorption rate, such as metabolic bone diseases, or bone lesions or metastases, and especially osteoporosis. The method of measuring the amount of TRAP 5b can also be used in monitoring the effect of treatment of bone diseases, e.g. the effect of estrogen or biphosphonate treatment of osteoporosis. It may also be used in screening people for susceptibility to increased bone resorption thereby enabling treatment to prevent bone fractures.

'Subject' as used in this connection means a mammal, preferably a human being.

'TRAP' as used in the present application refers to tartrate-resistant acid phosphatase (EC 3.1.3.2. ), which belongs to the type 5 class of acid phosphatases including both forms 5a and 5b of the enzyme.

'TRAP 5b' refers to the enzyme form b of TRAP lacking sialic acid in its carbohydrate chain and having a pH optimum between about 5.7 and 6.0.

'TRAP 5a' refers to the enzyme form a of TRAP comprising sialic acid in its carbohydrate chain and having a pH optimum at about 4.9.

Said enzymes are further described e.g. in Lam W. K. W. et al. (Clin. Chem. 24(7):1105–1108, 1978) and Lam W. K. W. et al. (Clin. Biochem. 14, 177–181, 1981).

The body fluid sample is preferably, but not necessarily, a blood sample, such as plasma or especially serum.

In the immunoassay of the invention antibodies against TRAP are used. By 'immunoassay' in this connection is meant any assay where the compound to be determined is detected by an antigen-antibody reaction. The immunoassay may be a direct or indirect, competitive or non-competitive assay. It may be a sandwich technique or a simple one. Either the antigen or the antibody can be labelled to enhance the detection. The principles of these methods are well known in the art.

'Antibodies against TRAP' as used in the present invention include both 5a and 5b non-specific and specific anti-TRAP antibodies.

The antibodies against TRAP are preferably monoclonal antibodies. Said monoclonal antibodies can be antibodies, which are capable of distinguishing between TRAP 5b and TRAP 5a. Antibodies 'capable of distinguishing between TRAP 5b and TRAP 5a' can be either TRAP 5b or TRAP 5a specific, or they may consist of any combination of said specific antibodies with antibodies recognizing the total TRAP, i.e. both TRAP 5b and TRAP 5a.

The antibodies capable of distinguishing between TRAP 5a and TRAP 5b can be used in several ways to determine the concentration of TRAP 5b in a body fluid. If antibodies specific to TRAP 5b are used, they can of course be used directly to detect TRAP 5b. However, it is preferrable that the TRAP 5b specific antibody is used in combination with an antibody, which recognizes both forms of enzymes, i.e. total TRAP. In that case the total TRAP of the body fluid may first be bound to the antibody recognizing both enzyme forms and then a labelled antibody, which is specific to TRAP 5b, but which does not react with TRAP 5a, is used to detect the bound TRAP 5b.

It is further possible to use a combination of antibodies specific to TRAP 5a and antibodies recognizing total TRAP. In that case TRAP 5a is first bound to the TRAP 5a specific antibodies and then the remaining unbound TRAP activity, which must be the form 5b, is determined using the antibodies recognizing both enzyme forms.

The antibodies used in the method of the invention can be labelled in any conventional way e.g with a radioactive label, an enzyme label, a chemiluminescence label, or a fluorescent label to enhance their detection. The streptavidin-biotinyl system provides a sensitive detection. Especially good results have been obtained using the Delfia system, which is a time-resolved fluoroimmunoassay described e.g. in Heilman J. et al. J. Bone Miner. Res. 1 1:1 165–1175, 1996; and Hemmila I. et al., Anal. Biochem. 137:335–343, 1984. It is further preferable to use at least two different antibodies, which recognize different epitopes of TRAP. This enables a highly sensitive and reproducible two-site fluoroimmunoassay.

The test-kit of the present invention comprises antibodies capable of distinguishing between TRAP 5b and TRAP 5a. This test-kit is useful in assessing the bone resorption rate and in diagnosing disorders associated with a change in the bone resorption rate according to the invention. The test-kit may comprise antibodies specifically recognizing TRAP 5b, optionally in addition with antibodies recognizing total TRAP. Alternatively the test-kit may comprise antibodies specifically recognizing TRAP 5a together with antibodies recognizing total TRAP, or it may comprise TRAP 5b specific antibodies and TRAP 5a specific antibodies. The antibodies are preferably monoclonal antibodies.

Another possibility to measure the TRAP 5b activity according to the present invention is to carry out a conventional spectrophotometric method for acid phosphatase activity in the presence of tartrate (see e.g. Halleen J. et al. Journal of Bone and Mineral Research 11(10):1444–1452, 1996) at a pH range, which is within the enzyme activity peak of TRAP 5b, but outside that of TRAP 5a. The pH optimum of TRAP 5a is about 4.9 and that of TRAP 5b is about 5.7 to 6.0 as measured by the inventors. Total TRAP is normally measured at pH 5.5. However, it was found that a suitable pH range for the determination of TRAP 5b in the presence of TRAP 5a is 5.7–6.3, preferably 5.8–6.2 and especially 6.0–6.2. A pH of 6.1 is the most preferable. Although the spectrophotometric method does not distinguish between TRAP 5a and TRAP 5b, the activity measured within said pH range is substantially TRAP 5b. The activity of TRAP 5a at pH 6.1 is only about 20–30 % of the activity at pH 4.9. (If TRAP 5b is determined in the absence of TRAP 5a, a slightly higher activity is achieved at a pH of about 5.9). At pH 6.1, the ratio of 5a activity to total TRAP activity is less than 10%. Thus, more than 90% of the measured TRAP activity at pH 6.1 is form 5b.

Taking advantage of the difference in the pH optimum of TRAP 5b and TRAP 5a in the immunoassay provides a cheap and simple method of determining TRAP 5b. This procedure enables the use of non-specific anti-TRAP antibodies (bind both 5a and 5b), which are first used to bind the total TRAP of the body fluid. Thereafter the TRAP activity is measured e.g. spectrophotometrically in the pH range between 5.7 and 6.3, which favours the TRAP 5b activity.

The difference in carbohydrate content can also be used in distinguishing between TRAP 5b and TRAP 5a. Total TRAP is for example first bound by antibodies recognizing both 5a and 5b. The bound total TRAP is then reacted with labelled Galanthus Nivalis Agglutinin (GNA) or Concanavalin A (ConA) lectin, which binds to carbohydrates having terminal mannose such as TRAP 5b, but which does not bind to TRAP 5a, since it has terminal sialic acid in its carbohydrate chain.

Of course it is possible to use any combination of the above-described procedures to determine TRAP 5b in the methods of the present invention. The invention is further described in the following non-limiting examples.

EXAMPLE 1

Monoclonal antibodies were produced using standard protocols. BALB/c mice were injected four times at 2-week intervals with (20 µg/mouse at a time) purified human bone TRAP (Halleen J. et al. Journal of Bone and Mineral Research 11(10):1444–1452, 1996), emulsified in Freund's adjuvant, after which the animals were killed. Spleen cells were hybridized with the myeloma cell line p3-X63-Ag8.653, and the hybridomas were cultured in HAT medium. Clones were screened by incubating 100 µl of supernatant in anti-mouse IgG-coated microtiter wells, followed by incubation of purified human bone TRAP. Finally, bound enzyme activity was determined by incubating 200 µl of reaction mixture (0.1 M sodium acetate, pH 6.0, 8 mM pNPP and 40 mM sodium tartrate) in wells for 1 hour. The reactions were stopped by adding 16 µl of 0.5 M sodium hydroxide. Absorbance at 405 nm was measured with an ELISA plate reader. Two monoclonal TRAP antibodies, O1A and J1B, were obtained. Both antibodies recognized both TRAP 5a and TRAP 5b, but different epitopes.

A monoclonal antibody 4E6 developed using recombinant TRAP as an antigen (Chamberlain P. et al. Clin. Chem. 41(10):1495–1499, 1995) was found not to react with TRAP isolated and purified from bone. Instead it was found to specifically recognize the sialic acid containing 5a form of TRAP. 400 ng of 4E6 was incubated for 1 h in anti-mouse IgG coated microtiter wells. Serum samples (200 µl) were then incubated for 1 h in the wells. As a control, samples from the same sera were similarly incubated in empty anti-mouse IgG coated microtiter wells. 50 µl triplicates were taken from the wells, and mixed with 100 µl of Delfia assay buffer containing 400 ng of europium-labelled O1A and biotinylated J1B. The mixtures were incubated for 2 h in streptavidin-coated microtiter wells with constant shaking in a Delfia plate shaker (1296-001 Delfia plateshaker, Wallac Oy, Turku, Finland), and then washed with Delfia wash buffer. Finally the wells were filled with Delfia enhancement solution, shaken for 5 minutes, and bound fluoresence was measured. This method is further described e.g. in Hellman J. et al. J. Bone Miner. Res. 11:1165–1175, 1996; and Hemmilä I. et al., Anal. Biochem. 137:335–343, 1984.

The results are summarised in Table 1. It was found that the amount of TRAP 5a was almost the same in premenopausal and postmenopausal women, but the difference in TRAP 5b amount between the two groups was significant. The specific determination of TRAP 5b compared with total TRAP thus significantly improved the usefulness of TRAP as a marker for bone resorption. It was also confirmed that the level of TRAP 5b is significantly higher in children than in adults, while the level of TRAP 5a is almost constant.

TABLE 1

The amount of TRAP (µg/l) in sera.

| Measured enzyme | Pre-menopausal women | Posmeno-pausal women | Children | Post/Pre[1] | Children/Pre[2] |
|---|---|---|---|---|---|
| Total TRAP | 12.44 | 18.06 | 30.89 | 1.45 | 2.48 |
| TRAP 5a | 6.42 | 6.76 | 7.22 | 1.05 | 1.12 |
| TRAP 5b | 6.03 | 11.29 | 23.67 | 1.87 | 3.93 |

[1]Post/Pre = the ratio of TRAP enzyme forms in postmenopausal women vs. premenopausal women
[2]Children/Pre = the ratio of TRAP enzyme forms in children vs. premenopausal women

EXAMPLE 2

Anti-mouse IgG -coated microtiter wells were pre-washed, and monoclonal TRAP-antibody O1A (400 ng of antibody/well) was incubated for 1 hour in the wells with constant shaking. The wells were washed, and serum samples from 40 healthy adults were incubated in the wells for 1 h with constant shaking. The wells were washed, and bound TRAP activity was measured by incubating 200 ml of a reaction mixture (0.1 M sodium acetate, pH 5.9, 8 mM pNPP and 40 mM sodium tartrate) in the wells for 1 hour. The reactions were stopped by adding 25 ml of 0.32 M sodium hydroxide. Absorbance at 405 nm was measured with an ELISA plate reader.

Based on the results two groups were formed: "High" which contained those eight samples having the highest total activity of TRAP and "Low", which contained those eight samples having the lowest total activity of TRAP. TRAP 5a and TRAP 5b were specifically determined in the two groups by first binding 5a to antibody 4E6 and then determining the unbound activity i.e. TRAP 5b with antibody O1A as described above. TRAP 5a activity was measured at pH 5.0 and TRAP 5b activity at pH 5.9. The results (absorbance at 405 nm) are shown in Table 2. It can be seen that both groups contained about the same amount of TRAP 5a, whereas the amount of TRAP 5b was remarkably higher in the High group.

TABLE 2

TRAP activity in high and low activity sera

| TRAP form | High (Mean ± SD) | Low (Mean ± SD) | High/Low |
|---|---|---|---|
| 5a | 0.414 ± 0.139 | 0.415 ± 0.089 | 0.998 |
| 5b | 0.610 ± 0.227 | 0.171 ± 0.043 | 3.550 |

Finally total TRAP from both groups was determined by binding to antibody O1A and the bound TRAP activity was measured as described above at different pH values. The results (absorbance at 405 nm) are shown in Table 3. The results clearly show that when the pH increases the difference between the two groups increases. The best difference (2.46) was achieved at pH 6.1.

TABLE 3

TRAP activity at different pH values

| pH | High (Mean ± SD) | Low (Mean ± SD) | High/Low |
|---|---|---|---|
| 5.0 | 0.786 ± 0.200 | 0.683 ± 0.116 | 1.15 |
| 5.5 | 0.738 ± 0.236 | 0.455 ± 0.078 | 1.62 |
| 5.9 | 1.085 ± 0.332 | 0.538 ± 0.088 | 2.02 |
| 6.1 | 0.931 ± 0.298 | 0.377 ± 0.085 | 2.46 |

EXAMPLE 3

The activity of serum TRAP 5a and TRAP 5b at different pHs was studied. This was done by binding TRAP 5a from serum samples using antibody 4E6, and then binding the remaining TRAP 5b using antibody O1A. Bound TRAP activity was measured as described in the first paragraph of example 2, except that the pH of the acetate buffer was changed as indicated. Table 4 shows the absorbance values ($A_{405}$) obtained for TRAP 5a and TRAP 5b at different pHs using pNPP as a substrate. Column % 5a indicates the ratio of 5a activity to total TRAP activity (5a+5b) at each pH, for example at pH 4.7, % 5a is 0.256/0.354=72%.

TABLE 4

| pH | 5a activity | 5b activity | % 5a | 5a + 5b |
|---|---|---|---|---|
| 4.1 | 0 | 0 | — | 0 |
| 4.3 | 0.032 | 0.023 | 58% | 0.055 |
| 4.5 | 0.187 | 0.045 | 80% | 0.232 |
| 4.7 | 0.256 | 0.098 | 72% | 0.354 |
| 4.9 | 0.317 | 0.188 | 62% | 0.505 |
| 5.1 | 0.266 | 0.477 | 35% | 0.743 |
| 5.3 | 0.243 | 0.504 | 32% | 0.747 |
| 5.5 | 0.211 | 0.549 | 27% | 0.760 |
| 5.7 | 0.158 | 0.570 | 21% | 0.728 |
| 5.9 | 0.103 | 0.583 | 15% | 0.686 |
| 6.1 | 0.057 | 0.552 | 9.3% | 0.609 |
| 6.3 | 0.033 | 0.308 | 9.6% | 0.341 |
| 6.5 | 0.016 | 0.143 | 10% | 0.159 |

Based on Table 4, pH 6.1 appears to be the best pH value for detecting TRAP 5b specifically, as the interference of TRAP 5a is very low (9.3%), while TRAP 5b is almost as active as in the pH optimum range (5.7–5.9). Usually, serum TRAP activity is detected using pH 5.5, because this is the optimum pH value observed when measuring total serum TRAP activity (which is due to the fact that the combined activity of TRAP 5a and TRAP 5b is highest at pH 5.5, as seen in the table above, column 5a+5b).

EXAMPLE 4

The TRAP 5b specific method of Example 3, where serum TRAP 5b activity bound to O1A is measured at pH 6.1 was then compared with a two-site assay, where total serum TRAP was determined by binding the TRAP to O1A and detecting the total TRAP by using the Delfia-system with europium-labeled J1B. Serum samples from a group of postmenopausal women (aged >70) were used to study the effect of a 6 months estrogen replacement therapy (HRT) on the serum TRAP amount. According to the TRAP 5b specific method there was a 48% drop in the TRAP 5b activity after 6 months HRT (p =0.001), whereas in the control-group (who received placebo instead of estrogen), a 2% increase in TRAP 5b activity was observed after 6 months. The two-site assay for total TRAP detected a 15–20% drop after 6 months in both groups. These results show that the two-site method measuring total TRAP is not sensitive in detecting changes in the bone resorption rate after 6 months HRT, whereas the method measuring specifically TRAP 5b detects an almost 50% decrease after 6 months HRT, suggesting that it is highly useful in monitoring HRT treatment of osteoporosis patients. Thus, TRAP 5b is a significantly better marker in detecting changes in the bone resorption rate during estrogen replacement therapy than the two-site assay measuring total TRAP. The results are shown in FIG. 1.

EXAMPLE 5

Figure 2:
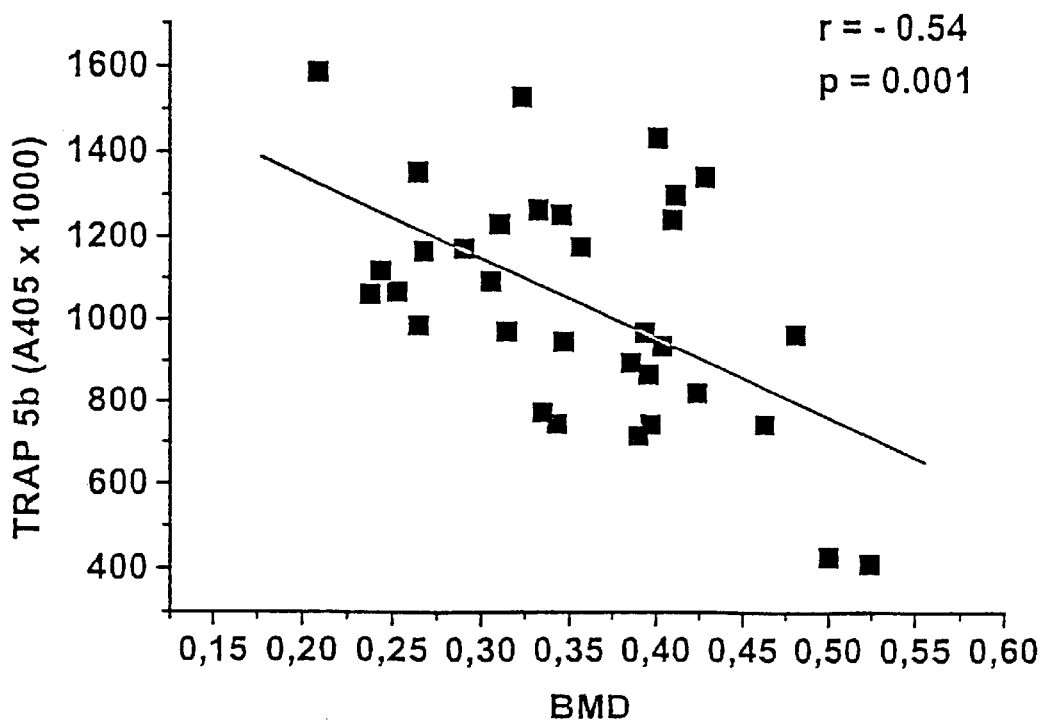
FIG. 2 shows the negative correlation between serum TRAP 5b and bone mineral density (BMD).

Finally, the correlation of the amounts of serum TRAP 5b and total serum TRAP to bone mineral density (BMD) was studied using a panel of serum samples of postmenopausal women. The results show that TRAP 5b has a significantly better negative correlation with BMD (r=−0.540, p=0.001, ***) than total TRAP (r=−0.156, p=0.1488, no significant correlation). FIG. 2 shows the correlation curve for TRAP 5b with BMD.

This data convincingly shows that serum TRAP 5b is a significantly more specific and sensitive marker of bone resorption rate than total serum TRAP.

What is claimed is:

1. An immunoassay for measuring the bone resorption rate in a subject, comprising the steps of
   (a) binding tartrate-resistant acid phosphatase TRAP present in a body fluid sample from said subject to an antibody that binds total TRAP, and
   (b) determining bound TRAP enzyme activity at a pH between 5.7 and 6.3, whereby the amount of bound TRAP activity reflects the amount of TRAP 5b activity, which in turn reflects the bone resorption rate.

2. The method of claim 1, wherein monoclonal antibodies against tartrate-resistant acid phosphatase TRAP are used in step (a).

3. The method of claim 2, wherein the bound TRAP activity is determined spectrophotometrically.

4. The method of claim 1, wherein the bound TRAP activity is determined at a pH of about 6.1.

5. The method of claim 1, wherein the body fluid sample is a serum sample.

6. An immunoassay for measuring the bone resorption rate in a subject, comprising the steps of
   (a) binding tartrate-resistant acid phosphatase TRAP 5a present in a body fluid sample from said subject to an antibody that binds TRAP 5a, and
   (b) determining unbound TRAP enzyme activity at a pH between 5.7 and 6.3, whereby the amount of unbound TRAP activity reflects the amount of TRAP 5b activity, which in turn reflects the bone resorption rate.

7. The method of claim 6, wherein monoclonal antibodies against tartrate-resistant acid phosphatase TRAP 5a are used in step (a).

8. The method of claim 7, wherein the unbound TRAP activity is determined spectrophotometrically.

9. The method of claim 6, wherein the unbound TRAP activity is determined at a pH of about 6.1.

10. The method of claim 6, wherein the body fluid sample is a serum sample.

11. A test-kit comprising antibodies against total tartrate-resistant acid phosphatase TRAP or against tartrate-resistant acid phosphatase TRAP 5a, a buffer having a pH between 5.7 and 6.3 and instructions for carrying out at least one of a
   method for measuring the bone resorption rate in a subject, comprising the steps of (a) binding tartrate-resistant acid phosphatase TRAP present in a body fluid sample from said subject to said antibodies that bind total TRAP, and
(b) determining bound TRAP enzyme activity at a pH between 5.7 and 6.3, whereby the amount of bound TRAP activity reflects the amount of TRAP 5b activity, which in turn reflects the bone resorption rate, or a method for measuring the bone resorption rate in a subject, comprising the steps of (a) binding tartrate-resistant acid phosphatase TRAP 5a present in a body fluid sample from said subject to said antibodies that bind TRAP 5a. and
(b) determining unbound TRAP enzyme activity at a pH between 5.7 and 6.3, whereby the amount of unbound TRAP activity reflects the amount of TRAP 5b activity, which in turn reflects the bone resorption rate.

* * * * *